US010667862B2

(12) United States Patent
Montague et al.

(10) Patent No.: US 10,667,862 B2
(45) Date of Patent: Jun. 2, 2020

(54) LASER-BASED SURGICAL SYSTEMS AND RELATED METHODS

(71) Applicant: Boston Scientific Scimed, Inc., Maple Grove, MN (US)

(72) Inventors: Matthew Montague, Galway (IE); Martyn G. Folan, County Galway (IE); Thomas M. Keating, Galway (IE); Paul E. Tierney, County Galway (IE); Martin Hynes, Galway (IE)

(73) Assignee: Boston Scientific Scimed, Inc., Maple Grove, MA (US)

( * ) Notice: Subject to any disclaimer, the term of this patent is extended or adjusted under 35 U.S.C. 154(b) by 722 days.

(21) Appl. No.: 15/351,630

(22) Filed: Nov. 15, 2016

(65) Prior Publication Data

US 2017/0143422 A1 May 25, 2017

Related U.S. Application Data

(60) Provisional application No. 62/257,927, filed on Nov. 20, 2015.

(51) Int. Cl.
  *A61B 18/20* (2006.01)
  *A61B 18/28* (2006.01)
  *A61B 18/00* (2006.01)

(52) U.S. Cl.
  CPC .............. *A61B 18/20* (2013.01); *A61B 18/28* (2013.01); *A61B 2018/00577* (2013.01); *A61B 2018/00589* (2013.01); *A61B 2018/206* (2013.01); *A61B 2018/2035* (2013.01)

(58) Field of Classification Search
  CPC .................... A61B 18/20; A61B 18/28; A61B 2018/00577–00607; A61B 2018/206
  See application file for complete search history.

(56) References Cited

U.S. PATENT DOCUMENTS

| | | | | |
|---|---|---|---|---|
| 5,496,309 A | * | 3/1996 | Saadat | A61B 18/24 606/15 |
| 5,562,657 A | * | 10/1996 | Griffin | A61B 18/245 606/13 |
| 6,239,190 B1 | | 5/2001 | Wilkinson et al. | |
| 6,530,944 B2 | | 3/2003 | West et al. | |
| 6,685,730 B2 | | 2/2004 | West et al. | |
| 7,909,817 B2 | * | 3/2011 | Griffin | A61B 18/22 606/13 |
| 9,061,056 B2 | | 6/2015 | Haris et al. | |
| 9,877,801 B2 | * | 1/2018 | Khakpour | A61C 17/20 |
| 2003/0093092 A1 | | 5/2003 | West et al. | |
| 2004/0034341 A1 | | 2/2004 | Altshuler et al. | |
| 2010/0042214 A1 | | 2/2010 | Nebosky et al. | |

(Continued)

*Primary Examiner* — Eric D. Bertram
(74) *Attorney, Agent, or Firm* — Bookoff McAndrews, PLLC

(57) ABSTRACT

According to one aspect, a medical system may include a laser source for providing laser energy. The medical system may also include a fluid source containing a fluid for absorbing the laser energy to generate heat. The medical system may further include a medical device operatively coupled to the laser source and the fluid source. The medical device may include a shaft having a distal end, and a cap at the distal end of the shaft. The cap may include a lens and a reflector for deflecting the laser energy toward the lens. The lens may be configured to emit the laser energy from the cap toward a target.

20 Claims, 3 Drawing Sheets

(56) References Cited

U.S. PATENT DOCUMENTS

2010/0160904 A1* 6/2010 McMillan .............. A61B 18/22
 606/16
2012/0220991 A1 8/2012 Jenny et al.
2013/0053832 A1 2/2013 Lewinsky et al.
2014/0025033 A1 1/2014 Mirkov et al.
2014/0031805 A1 1/2014 Shadduck

* cited by examiner

LASER-BASED SURGICAL SYSTEMS AND RELATED METHODS

CROSS-REFERENCE TO RELATED APPLICATIONS

This application claims the benefits of priority from U.S. Prov. App. No. 62/257,927, filed on Nov. 20, 2015, the entirety of which is herein incorporated by reference.

TECHNICAL FIELD

Various aspects of the present disclosure relate generally to laser-based surgical systems and related methods. More specifically, the present disclosure relates to endoscopic laser-based surgical systems and related methods for delivering laser energy to a target site and/or enhancing absorption of laser energy at the target site.

BACKGROUND

A wide variety of endoscopic surgical systems and methods may be used to treat tissue. With these systems and methods, an endoscope may be inserted into a subject and navigated to a target site. An instrument may be inserted through the endoscope to the target site, and may be used to treat tissue at the target site. One type of instrument that may be used to treat the tissue may use laser energy to vaporize the tissue. It may be difficult for a user of such an instrument to precisely direct the laser energy into, through, and/or around the tissue, depending on the location and dimensions of the tissue being treated. The difficulty may be exacerbated by movement of the subject, a limited availability of space in the subject's body, and tissue characteristics that may hinder laser energy absorption. As such, the laser energy may not be able to generate sufficient heat at the tissue to cause vaporization. Systems and methods that facilitate laser energy delivery to the tissue, and/or absorption of laser energy by the tissue, may improve outcomes.

SUMMARY

In one aspect of the present disclosure, a medical system may include a laser source for providing laser energy. The medical system may also include a fluid source containing a fluid for absorbing the laser energy to generate heat. The medical system may further include a medical device operatively coupled to the laser source and the fluid source. The medical device may include a shaft having a distal end, and a cap at the distal end of the shaft. The cap may include a lens and a reflector for deflecting the laser energy toward the lens. The lens may be configured to emit the laser energy from the cap toward a target.

Aspects of the medical system may include one or more of the features below. The shaft may include a lumen, the laser source may extend through the lumen, and the laser source may deliver laser energy into the cap. The laser source may include a laser fiber that extends out of the distal end of the shaft into the cap. The lens may be embedded in a wall of the cap. The cap may include a lumen, and the reflector may be supported within the lumen by a wall of the cap forming the lumen. The fluid may include an additive that absorbs a wavelength of light forming part of the laser energy. The fluid may absorb enough of the laser energy so that the fluid builds heat faster than heat can be dissipated to the external environment. The shaft may include a lumen in fluid communication with the fluid source, and the cap may include a lumen in fluid communication with the lumen of the shaft. The fluid may flow from the fluid source into the lumen of the shaft, into the lumen of the cap, and out of the lumen of the cap for emission toward the target.

In another aspect of the present disclosure, a medical device may include a shaft including a distal end. The medical device may also include a cap at the distal end of the shaft. The cap may include a lens and a reflector for deflecting laser energy toward the lens. The lens may be configured to emit laser energy from the cap toward a target. The cap may also include an aperture for emitting a fluid from the cap toward the target.

Aspects of the medical device may include one or more of the features below. The lens may be embedded in a wall of the cap. The cap may include a lumen, and the reflector may be supported within the lumen by a wall of the cap forming the lumen. The shaft may include a lumen in fluid communication with the aperture. The cap may include a lumen terminating at the aperture. The aperture may be on a radially-outer lateral surface of the cap. The lens may be one of a plurality of lenses in the cap. The reflector may be one of a plurality of reflectors in the cap.

In yet another aspect of the present disclosure, a method for endoscopic treatment of tissue in a subject may include inserting an endoscope having a shaft, and a cap mounted on the distal end of the shaft, into the subject. The method may also include maneuvering the shaft and the cap to the tissue. The method may also include introducing a fluid onto or into a portion of the tissue. The method may also include emitting laser energy from the cap toward the tissue. The fluid may absorb the laser energy to create a hyperthermic region on or in the portion of the tissue.

Aspects of the method may include one or more of the features below. The hyperthermic region may form a cut in the portion of the tissue. The hyperthermic region may ablate or coagulate the portion of the tissue.

It may be understood that both the foregoing general description and the following detailed description are exemplary and explanatory only and are not restrictive of the features claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn generally to laser-based surgical systems and related methods, and more specifically to endoscopic laser-based surgical systems and related methods for delivering laser energy to a target site of tissue and/or enhancing absorption of laser energy by the target site of tissue. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject. The term "approximately," when used to describe a numerical value, may be anywhere in a range of ±5% from the numerical value.

Figure 1A:
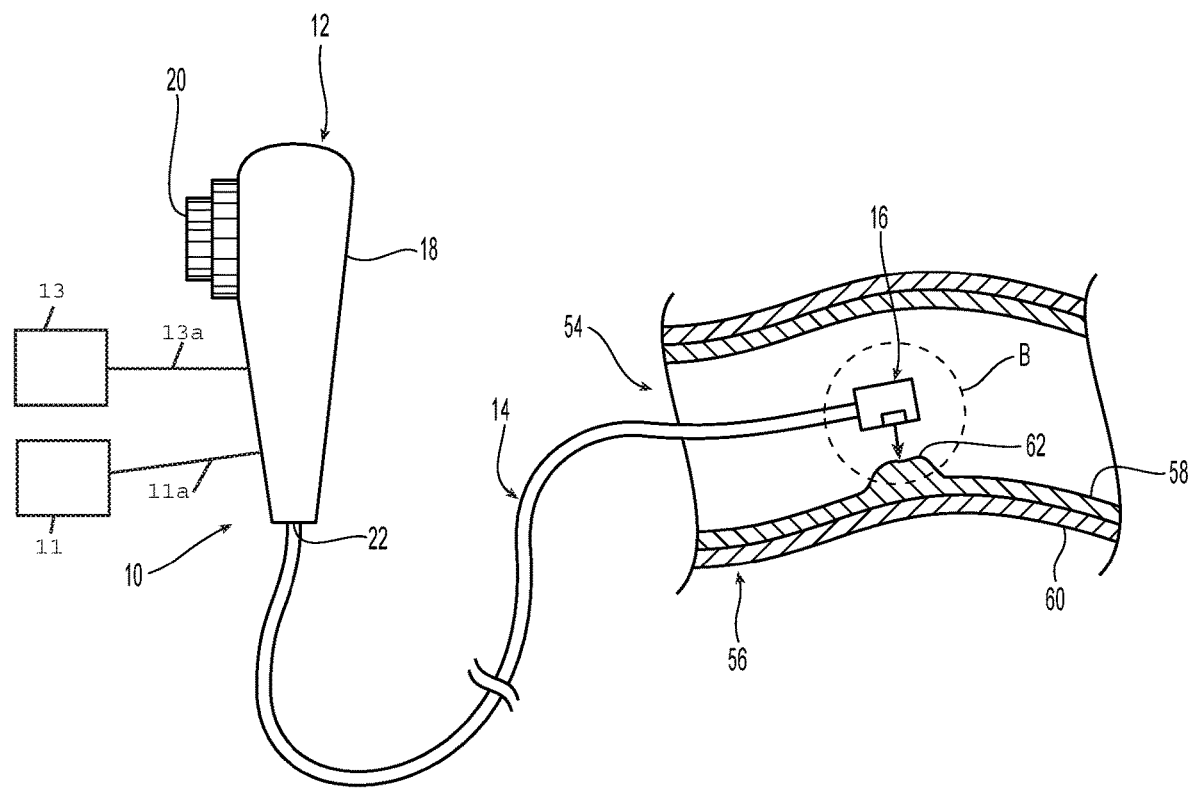
FIG. 1A is a schematic view of a laser-based surgical system in use, in accordance with aspects of the present disclosure.
Figure 1B:
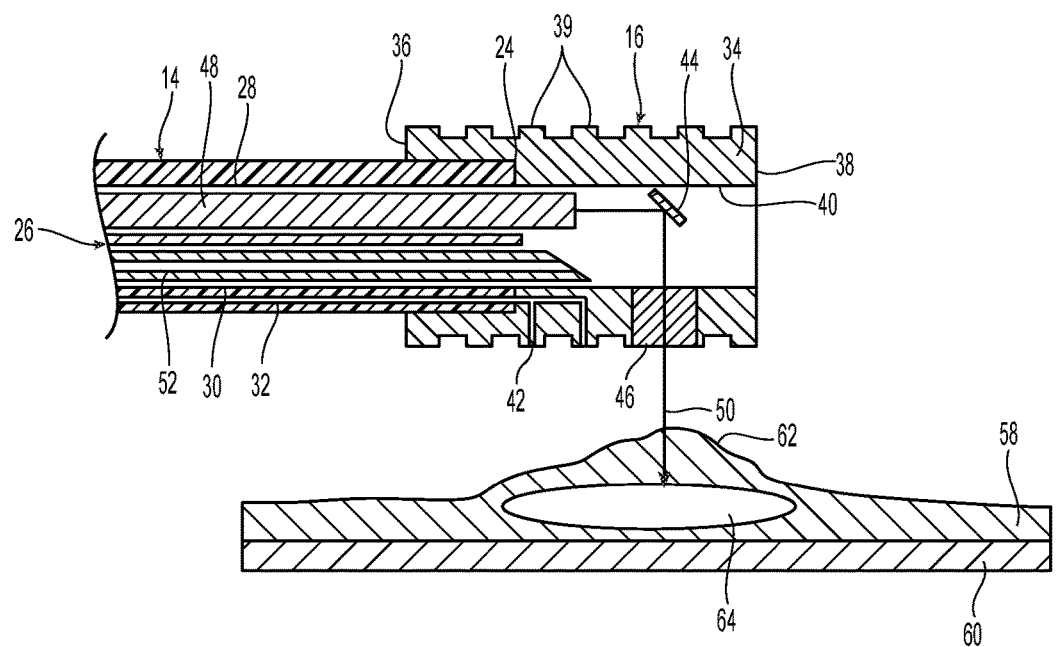
FIG. 1B is a partial side cross-sectional view of a portion of the laser-based surgical system of FIG. 1A, in accordance with aspects of the present disclosure.

FIGS. 1A and 1B show aspects of an endoscope system 10. Endoscope system 10 may include, for example, a handle 12, a shaft 14, and a cap 16. Handle 12 may be coupled to a proximal end 22 of shaft 14. Cap 16 may be coupled to a distal end 24 of shaft 14. In use, handle 12 may remain outside of a subject, while cap 16 and at least a portion of shaft 14 may be inserted into the subject. Handle 12 may include a housing 18 that may be gripped by a user. Handle 12 may also include controls 20 accessible to the user while the user grips housing 18. Controls 20 may be used to manipulate one or more steering wires (not shown) that may extend through housing 18 and into shaft 14. The steering wires may be coupled to distal end 24 of shaft 14 and/or cap 16, such that by manipulating the steering wires with controls 20, the user may deflect distal end 24 and cap 16. The deflection may assist with inserting shaft 14 and cap 16 into the subject, navigating shaft 14 and cap 16 through the subject, and/or orienting cap 16 at or near an area of tissue. For example, shaft 14 and cap 16 may be positioned in an anatomical structure 54 of the subject, with cap 16 at or adjacent a target site 62 of tissue 56. Tissue 56 may include one or more layers (a first layer 58 and a second layer 60 being depicted in FIGS. 1A and 1B). Target site 62 may include a lesion or polyp on or within first layer 58 that the user may be seeking to treat. According to one aspect, anatomical structure 54 may include the subject's colon. Alternatively, anatomical structure 54 may include any other lumen, cavity, organ or other structure in the subject's body.

Shaft 14 may include one or more internal lumens 26. For example, shaft 14 may include a first lumen 28, a second lumen 30, and a third lumen 32. It should be understood, however, that more or fewer internal lumens may be provided. Each of first, second, and third lumens 28, 30, and 32 may provide a pathway for an instrument to move through shaft 14 and/or for a fluid to flow proximally or distally through shaft 14.

Cap 16 may be mounted on or otherwise coupled to distal end 24 of shaft 14. For example, cap 16 may slide over and around distal end 24. Cap 16 may be secured to distal end 24 by friction fit, use of adhesive, and/or any other suitable form of securement. Alternatively, cap 16 may be integral with distal end 24. Cap 16 may include a body 34. In one example, body 34 may be cylindrical, but any suitable shape may be used. Body 34 may have a proximal end 36, a distal end 38, and a central lumen 40 extending between proximal end distal ends 36 and 38. Central lumen 40 may be in fluid communication with one or more internal lumens 26 of shaft 14. For example, central lumen 40 may be in fluid communication with first and second lumens 28 and 30, such that instruments moving distally along shaft 14 through first and second lumens 28 and 30 may extend out of distal end 24 of shaft 14 and into central lumen 40.

Body 34 may also include a peripheral lumen 42. Peripheral lumen 42 may extend through material forming body 34 in between radially inner and outer surfaces of body 34. Peripheral lumen 42 may be in fluid communication with one or more internal lumens 26 of shaft 14. For example, a proximal end of peripheral lumen 42 may be in fluid communication with a distal end of third lumen 32 of shaft 14. A distal end of peripheral lumen 42 may open at the radially outer surface of body 34. Peripheral lumen 42 may be in fluid communication with a fluid source, such that peripheral lumen 42 may emit fluid from the source out of cap 16. Additionally or alternatively, peripheral lumen 42 may be in fluid communication with a suction source, such that peripheral lumen 42 may be used to create a suction force on tissue 56 to raise or otherwise move tissue 56 with cap 16, and/or to remove fluid from tissue 56. It is also contemplated that peripheral lumen 42 may be branched, as shown in FIG. 1B, or alternatively, may be an unbranched continuous lumen. Further, while a single peripheral lumen 42 is shown in FIG. 1B, peripheral lumen 42 may be one of a plurality of peripheral lumens extending within body 34.

Cap 16 may also include a reflector 44 and a lens 46. Lens 46 may be coupled to a side portion of body 34, and may extend from the radially inner surface to the radially outer surface of body 34. According to one aspect, lens 46 may be embedded in material forming body 34. Reflector 44 may be coupled to body 34 at, for example, the radially inner surface of body 34 that surrounds lumen 40. Reflector 44 may include a mirror or any other suitable surface for reflecting light. Reflector 44 may be oriented so as to reflect light toward lens 46. Lens 46 may refract the reflected light from reflector 44. For example, lens 46 may include a convex or converging lens that refracts the reflected light toward a focal point, thus emitting concentrated light from cap 16. Alternatively, lens 46 may include a concave or diverging lens that refracts the reflected light away from a focal point, thus emitting diffused light from cap 16.

Body 34 of cap 16 may include corrugations 39 on its radially outer surface. Corrugations 39 may enhance the flexibility of body 34. Due to corrugations 39 and/or the characteristics of the material forming body 34, body 34 may be bent during use. This bendability may facilitate navigation of cap 16 through the subject, particularly in tight confines in, through, and/or around the subject's anatomical structures, where rigidity may impede or inhibit movement of cap 16. It is contemplated that Pebax or polyurethane may be used to form cap 16.

FIG. 1B shows a laser emitter 48 that may be received in first lumen 28 of shaft 14. A proximal end of laser emitter 48 may be operatively coupled to a laser source 11 (see FIG. 1A), the laser source being configured to generate laser energy having a desired wavelength and introduce the laser energy into laser emitter 48. Any suitable laser source may be used, and laser source 11 may be operatively coupled to laser emitter 48 by an optical fiber 11a via handle 12, as shown in FIG. 1A. For example, a near IR diode laser source that emits light in the 808 nm to 980 nm range may be used. Alternatively, a Neodymium:YAG laser source that emits light at 1064 nm may be used. Alternatively, a holmium: YAG (Ho:YAG) laser source may be used, which is a solid-state, pulsed laser source that emits light at a wavelength of approximately 2100 nanometers. Alternatively, carbon dioxide lasers which may emit light in the far IR spectrum of approximately 10.6 um may be used. This wavelength may react directly with the colorectal tissue aiding in polypoid resection. In some instances, such lasers may produce sufficient heating for resection even without the assistance of laser energy absorbing materials introduced into the tissue. This listing is not meant to be exhaustive and other laser sources for emitting light at other wavelengths may also be used.

Laser emitter 48 may include a flexible optical fiber that may transmit the laser energy from its proximal end to its distal end via internal reflection, and may emit the laser energy in the form of a laser beam 50 from the distal end. Reflector 44 may reflect laser beam 50 through lens 46 and out of cap 16. The emitted laser beam 50 may be used to dissect, resect, ablate, coagulate, and/or otherwise treat target site 62 of tissue 56, as described in more detail below.

FIG. 1B also shows components for delivering a fluid 64 to tissue 56. According to one aspect, a fluid injector 52 may be received in second lumen 30 of shaft 14. Fluid injector 52 may include, for example, a hypotube having a sharp distal end for penetrating tissue. Fluid injector 52 may be extended distally out of shaft 14 and cap 16 to penetrate tissue distal to cap 16, and/or fluid injector 52 may be extended distally out of shaft 14 to penetrate tissue drawn into central lumen 40 of cap 16 by suction provide by one of internal lumens 26. A fluid source 13 of fluid 64 may supply fluid 64 into fluid injector 52 for injection into the penetrated tissue. The penetrated tissue may include tissue 56, and fluid 64 may be injected into tissue 56 at, around, adjacent to, and/or below target site 62. Fluid source 13 may be connected to handle 12 via a fluid lumen 13a, e.g., a hose, to supply fluid to components of shaft 14, e.g., third lumen 32 or fluid injector 52, as shown in FIG. 1A.

Additionally or alternatively, peripheral lumen 42 may emit fluid 64. For example, the source of fluid 64 may introduce a high-pressure volume of fluid 64 into third lumen 32 of shaft 14. The high-pressure volume of fluid 64 may enter peripheral lumen 42, and then may be emitted out of cap 16 through the distal end of peripheral lumen 42. The pressure of the emitted fluid 64 may be sufficient to form a jet of fluid 64 that may penetrate tissue. The penetrated tissue may include tissue 56, and fluid 64 may be injected into tissue 56 at, around, and/or below target site 62.

Figure 3A:
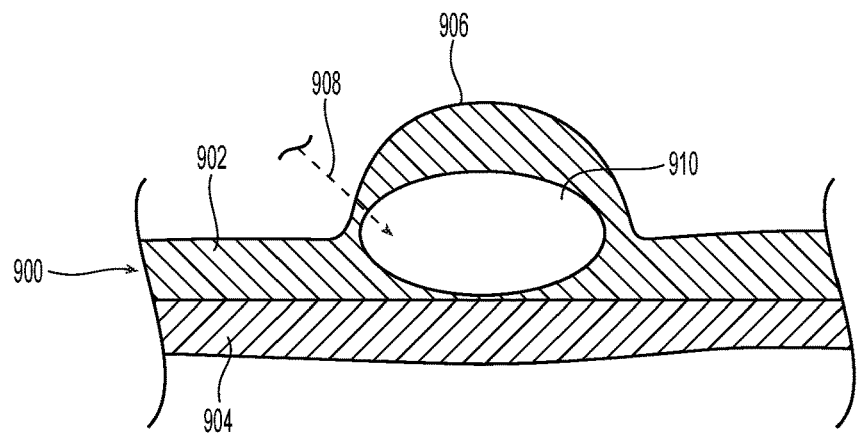
FIGS. 3A-3C are side cross-sectional views of target sites of tissue where a fluid may be administered, in accordance with aspects of the present disclosure.
Figure 3B:
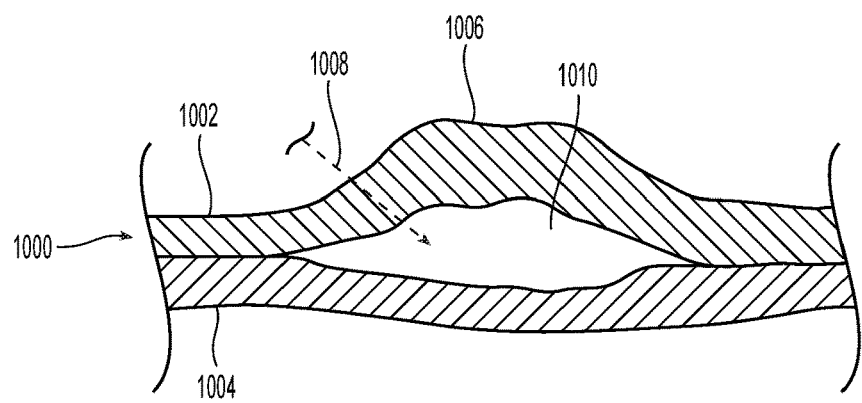

FIGS. 1B, 3A, and 3B depict the application of fluids to tissue. As shown in FIG. 1B, fluid 64 may form a pocket in first layer 58. FIG. 3A is similar to FIG. 1B, and shows a fluid 910 (which may be similar to fluid 64) injected along a flow path 908 into tissue 900 to form a pocket in tissue 900 (e.g., in a first layer 902 of tissue 900). The pocket may have a volume sufficient to raise a target site 906 away from other portions of first layer 902 and/or second layer 904. In FIG. 3B, a fluid 1010 (which may also be similar to fluid 64) may be injected along a flow path 1008 into tissue 1000 to form a pocket between first and second layers 1002 and 1004 to raise target site 1006. However, it should be understood that while pockets of fluids 64, 910, and 1010 are depicted in FIGS. 1B, 3A, and 3B, fluids 64, 910, and 1010 may be absorbed into or otherwise migrate through tissue 56, 900, and 1000, leading to a partial or complete reduction in volume of the pockets. The absorption or migration of fluid 64 may form a zone of fluid-containing tissue in tissue 56 that may extend, for example, from the pocket below target site 62 toward a top surface of first layer 58, from the pocket up into target site 62, and/or from the pocket into areas around target site 62.

Figure 3C:
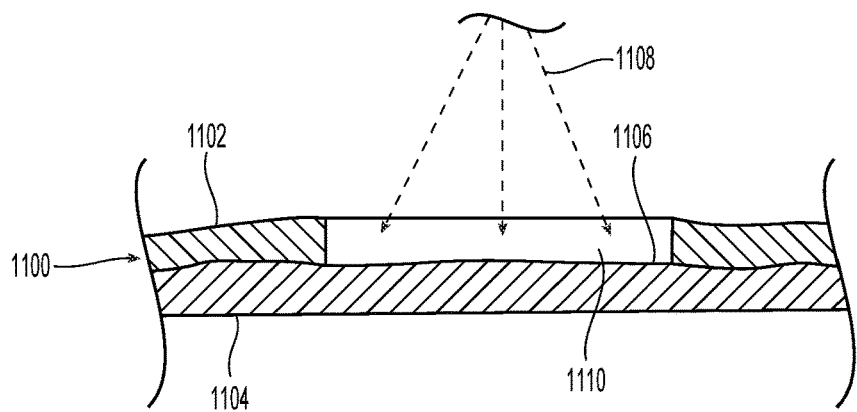

In another example, the source of fluid 64 may introduce a low-pressure volume of fluid 64 into third lumen 32, which may be emitted out of cap 16 through peripheral lumen 42 in the form of a spray. As such, fluid 64 may be sprayed onto a surface of tissue 56. The surface may include a surface of first layer 58, second layer 60, and/or target site 62. FIG. 3C shows a fluid 1110 (which may be similar to fluid 64) applied in spray form 1108 onto tissue 1100. Fluid 1110 may, for example, be sprayed onto margins around a portion of a first layer 1102 that was previously removed, and also onto an exposed portion of second layer 1104. Fluid 1110 may coat the surfaces of tissue 1100 when sprayed thereon, and/or may be absorbed into, or may otherwise migrate into, tissue 1100 to form zones of fluid-containing tissue. Additionally or alternatively, fluid may be delivered into and/or onto tissue using an injector (not shown) or sprayer (also not shown) external to and/or separate from endoscope system 10.

Fluid 64 may include a laser energy absorbing material for converting laser energy, such as that from laser beam 50, into heat. For example, the laser energy absorbing material may allow fluid 64 to absorb enough of the laser energy that fluid 64 may become hotter. By absorbing the laser energy, fluid 64 may act as a focal point for laser beam 50, which may result in controlled localized heating of tissue 56 in, at, and or adjacent fluid 64. The controlled localized heating may produce a hyperthermic region where desired, while reducing risk of thermal damage to surrounding tissue. Additionally or alternatively, the hyperthermic region may have enough heat to vaporize, cut, ablate, and/or coagulate tissue in and/or around the hyperthermic region. One example of a laser energy absorbing material is an infrared absorption fluid such as CLEARWELD®. For example, the CLEARWELD® 900 series is formulated to absorb laser wavelengths in the near IR spectrum range of between about 940 nm and 980 nm, and may be used for biomedical and food related applications. Other forms of laser absorption fluid technologies can include additive, pigmented or dyed microparticle/nanoparticle polymer solutions.

While many fluids that do not have laser energy absorbing material therein may also absorb at least some laser energy and may become hotter, the lack of laser energy absorbing material may result in those fluids not absorbing enough of the laser energy to overcome dissipation of the heat into the external environment. Or, the fluids may absorb enough laser energy to become hotter, but not enough heat to facilitate vaporizing, cutting, ablating, and/or coagulating tissue. In other words, with such fluids, the desired hyperthermic region may not be achievable.

The effectiveness of fluid 64 in absorbing laser energy may depend on a number of factors. For example, the effectiveness may depend upon a compatibility of fluid 64 with tissue 56, color of fluid 64 and/or tissue 56, density of tissue 56, level of opacity of tissue 56, wavelength of the laser energy, intensity of the laser energy, and/or any other parameters that may affect light absorption. The characteristics of laser beam 50 and/or of fluid 64 may be varied to achieve desired results. For example, additives may be incorporated, giving fluid 64 the ability to absorb laser energy of different wavelengths and/or intensities. Additionally or alternatively, additives may be added to increase viscosity of fluid 64 to slow the migration of fluid 64 away from target site 62, thus keeping more fluid 64 at target site 62 for a longer period of time for absorbing laser beam 50. Additionally or alternatively, the laser source or laser emitter 48 may be switched out for a different type, its operational wavelength may be modified, and/or its operational intensity may be adjusted.

The user may also control the effect of laser beam 50 on tissue 56 in other ways. For example, the user may inject fluid 64 into tissue 56 or spray fluid 64 onto tissue 56 in a pattern forming, for example, one or more pockets, lines, and/or curves. The injected fluid 64 may form one or more fluid pockets and/or zones of fluid-containing tissue in tissue 56. When laser beam 50 is directed at tissue 56, portions of tissue 56 in, at, or adjacent to fluid 64 may be heated sufficiently by absorption of laser beam 50 by fluid 64 to treat (e.g., cut, ablate, or coagulate) the portions of tissue 56. Other portions of tissue 56 further away from fluid 64 may be heated to a lesser degree when exposed to laser beam 50, or may remain untreated.

According to one example, the pattern of fluid 64 may surround a perimeter of target site 62, and/or may extend beneath target site 62. When laser beam 50 is directed at target site 62, the pattern of fluid 64 may form a corresponding pattern of cuts, thus resecting target site 62 from tissue 56. This approach may prevent target site 62 from being damaged or destroyed, in case the user may want to use target site 62 as a biopsy sample. The length and width of the sample may be controlled through the positioning of fluid 64 in a direction parallel to the surface of tissue 56, and/or the depth or height of the sample may be controlled through the positioning of fluid 64 in a direction perpendicular to the surface of tissue 56.

In another example, the pattern of fluid 64 may cover the surface of target site 62. When laser beam is directed at target site 62, the pattern of fluid 64 may form an ablation zone at target site 62, thus damaging or destroying target site 62. It is also contemplated that fluid 64 may be applied to exposed margins of tissue 56 after removal of target site 62 (e.g., in the manner shown in FIG. 3C). When laser beam 50 is applied, fluid 64 may form a coagulation zone to reduce bleeding at the exposed margins.

Another way of controlling the effect of laser beam 50 on tissue 56 may include using multiple types of fluid during a single procedure. For example, a first type of fluid may be applied to tissue 56 to facilitate resection of target site 62 using laser beam 50. Subsequently, a second type of fluid having at least one different characteristic from the first type of fluid, may be sprayed on the margins of tissue 56 left exposed by resection of target site 62. The first type of fluid may have one or more characteristics tailored to facilitate resection when exposed to laser beam 50, while the second type of fluid may have one or more different characteristics tailored to facilitate ablation or coagulation when exposed to laser beam 50. For example, the first type of fluid may be more absorptive of laser energy than the second type of fluid. When multiple types of fluid are used, one fluid may be removed by suction force from peripheral lumen 42 prior to application of another fluid. Alternatively, the fluid may not be removed and may be mixed with the other fluid.

Yet another way of controlling the effect of laser beam 50 on tissue 56 may include controlling one or more characteristics of laser beam 50. For example, lens 46 may cause laser beam 50 to converge toward a focal point. The converged laser beam 50 may be used to heat a small zone of tissue 56 in, at, and/or around fluid 64. This may provide for precision cutting of tissue 56. Alternatively, lens 46 may cause laser beam 50 to diverge and thereby heat a larger zone of tissue 56 in, at, and/or around fluid 64. This may provide for ablation or coagulation of a swath of tissue 56. Additionally or alternatively, lens 46 may shape laser beam 50 emitted onto tissue 56. For example, lens 46 may include one or more opaque portions such that the laser energy that is emitted is in the form of a linear laser beam with an ability to form a linear cut, ablation zone, and/or coagulation zone. Other laser beam shapes are also contemplated. Portions of tissue 56 outside of the hot zone created by laser beam 50 and fluid 64 may be heated to a lesser temperature or not heated at all. Moving laser beam 50 relative to tissue 56 (e.g., via translation, rotation, and/or pivoting of cap 16) may provide additional degrees of control over defining the treated area.

The intensity and/or wavelength of laser beam 50 may also be adjusted to facilitate absorption by fluid 64. For example, while fluid 64 may absorb a first range of wavelengths of light energy when separate from tissue 56, tissue 56 may affect that absorption once fluid 64 is introduced into tissue 56. This may be due, for example, to the color, density, or thickness of tissue 56. The wavelength of laser beam 50 may be adjusted to a second range of wavelengths to facilitate absorption by fluid 64 within tissue 56. Additionally or alternatively, the intensity of laser beam 50 may be increased or decreased to achieve the desired effect.

FIGS. 2A-2H show examples of caps that may be used with endoscope system 10 in place of cap 16. A cap 100 of FIG. 2A may include a body 102 similar to body 34 of cap 16 in FIG. 1B. Cap 100 may include a first reflector 104 and a first lens 108. First reflector 104 may include an electrochromic mirror whose optical properties may change under the influence of an electric field. The mirror may have multiple modes of operation, including a transmission mode in which the mirror is transparent and allows light to pass therethrough, and a reflection mode in which the mirror is opaque and reflects light. When first reflector 104 is in the reflection mode, a first laser beam 112 may be emitted from a side of cap 100 as laser energy is reflected off first reflector 104 and into first lens 108. When first reflector 104 is in the transmission mode, the laser energy may pass through first reflector 104 and reflect off second reflector 106. The reflected laser energy may pass through second lens 110, resulting in emission of a second laser beam 114 from the side of cap 100.

First lens 108 and second lens 110 may have one or more different characteristics. For example, first lens 108 may include a convex lens for converging first laser beam 112, making first laser beam 112 more suitable for dissecting and/or resecting tissue. Second lens 110 may include a concave lens for diverging second laser beam 114, making second laser beam 114 more suitable for ablating and/or coagulating tissue. Additionally or alternatively, one lens may be more/less transmissive than the other lens, and/or one lens may produce a differently shaped laser beam than the other. The effect is that the emissions from cap 100 may be selectively modified to perform a greater variety of procedures by switching first reflector 104 between its two modes of operation.

Figure 2A:
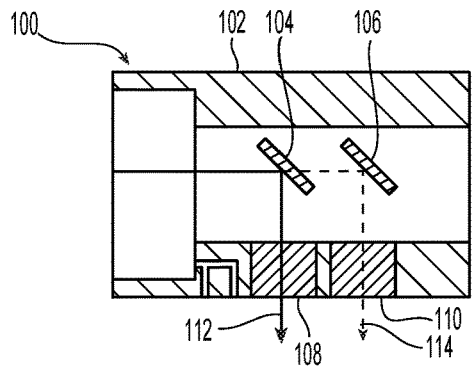
FIGS. 2A-2H are side cross-sectional views of cap assemblies for laser-based surgical systems, in accordance with aspects of the present disclosure.
Figure 2B:
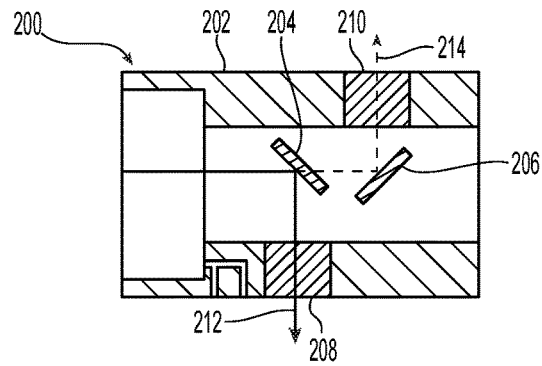

A cap 200 of FIG. 2B may include a body 202, first reflector 204, first lens 208, second reflector 206, and second lens 210, for producing a first laser beam 212 and a second laser beam 214, which may be similar to corresponding elements of cap 100 of FIG. 2A. With cap 200, however, second lens 210 may be on a side of body 202 opposite first lens 208. The orientation of second reflector 206 may be modified to direct laser energy toward second lens 210. Thus, with cap 200, first and second laser beams 212 and 214 may be emitted from different locations of cap 200. For example, first and second laser beams 212 and 214 may be emitted from diametrically opposite sides of cap 200. It should be understood, however, that other positional relationships for first and second lenses 208 and 210 are also contemplated.

Figure 2C:
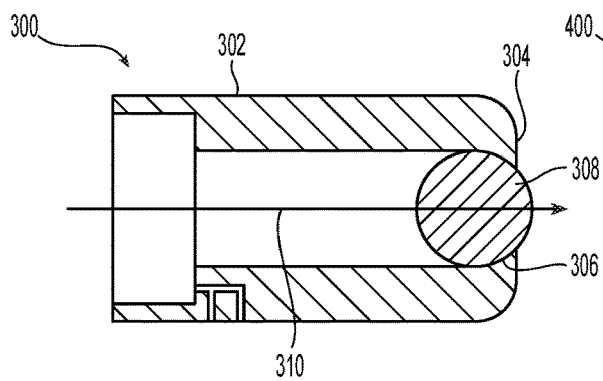

A cap 300 of FIG. 2C may include a body 302 that may be similar to body 34 of cap 16 in FIG. 1B. Cap 300, however, may have a distal end 304 that includes a portion 306 with a radially inwardly taper. Portion 306 may support a lens 308. Lens 308 may be spherical, and may be movably supported by portion 306 such that lens 308 may rotate. The spherical shape and rotation ability of lens 308 may facilitate navigation of cap 300 through the subject. The roller ball lens may help facilitate maximum contact with tissue by responding to the natural contours and folds of anatomical structures, and to different surface geometries presented by various types of polypoids. A laser beam 310 may be emitted from lens 308 and out beyond distal end 304.

Figure 2D:
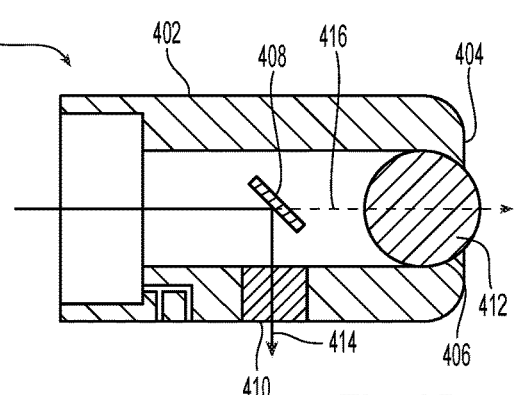

A cap 400 of FIG. 2D may include a body 402, distal end 404, tapered portion 406, and lens 412 similar to corresponding elements of cap 300 in FIG. 2C. Cap 400 may also include a reflector 408 and another lens 410 similar to reflector 104 and lens 108 of cap 100 in FIG. 2A. When reflector 408 is in a reflection mode, a first laser beam 414 may be emitted from a side of cap 400 as laser energy is reflected off reflector 408 and into lens 410. When reflector 408 is in a transmission mode, the laser energy may pass through reflector 408 and into lens 412, resulting in emission of a second laser beam 416 from distal end 404 of cap 400.

Figure 2E:
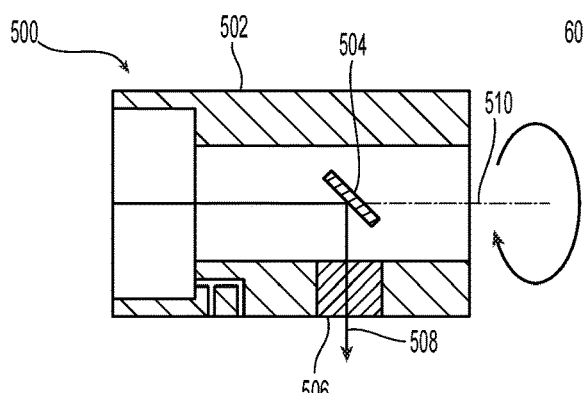

A cap 500 of FIG. 2E may include a body 502, reflector 504, and lens 506 similar to corresponding elements of cap 16 in FIG. 1B. Reflector 504 may be positioned along a central axis 510 of cap 500. A laser beam 508 may be reflected off reflector 504 and into lens 506 in a first direction. If the user wishes to change the emission direction of laser beam 508, the user may rotate cap 500 and reflector 504 about central axis 510. The user may rotate cap 500 and reflector 504 anywhere in a 360 degree arc about central axis 510, and accordingly, laser beam 508 may also be directed along the 360 degree arc.

Figure 2F:
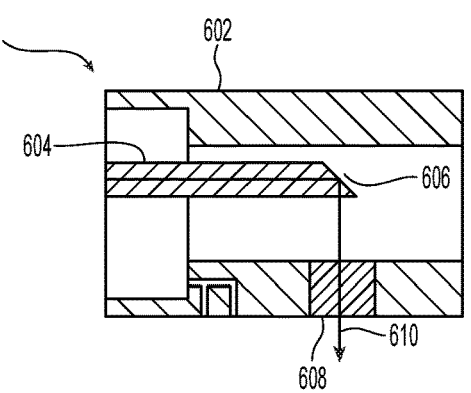

A cap 600 of FIG. 2F may include a body 602 and a lens 608 similar to corresponding elements of cap 16 in FIG. 1B. A laser fiber 604 having a distal reflective surface 606 may extend into cap 600. Laser energy may be transmitted through laser fiber 614 via internal reflection, and may reflect off reflective surface 606 into lens 608. Lens 608 may emit a laser beam 610 toward tissue. With such an arrangement, a separate mirror mounted on body 602 may be omitted. Further, the laser emission from cap 600 may be modified simply by replacing laser fiber 604 with another laser fiber.

Figure 2G:
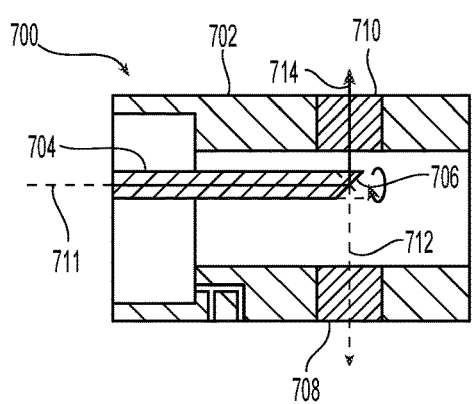

A cap 700 of FIG. 2G may include a body 702 and lenses 708 and 710 similar to corresponding elements of cap 200 in FIG. 2B. A laser fiber 704 with a distal reflective surface 706, similar to corresponding elements in FIG. 2F, may extend into cap 700. With laser fiber 704 in a first orientation, a first laser beam 714 may be emitted from a side of cap 700 as laser energy is reflected off reflective surface 706 and into lens 710. Laser fiber 704 may be rotated about a central axis 711 of cap 700 to a second orientation. In the second orientation, a second laser beam 712 may be emitted from another side of cap 700 as laser energy is reflected off reflective surface 706 and into the other lens 708.

Figure 2H:
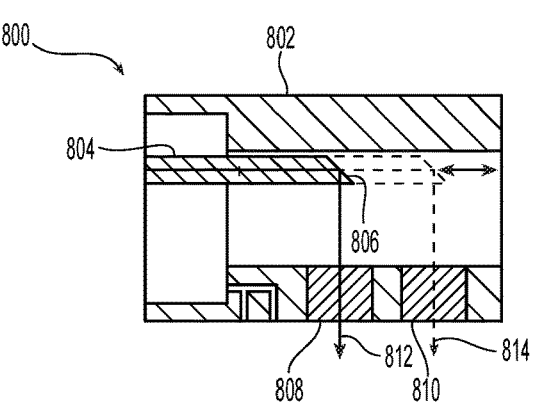

A cap 800 of FIG. 2H may include a body 802 and lenses 808 and 810 similar to corresponding elements of cap 100 of FIG. 2A. A laser fiber 804 with a distal reflective surface 806, similar to corresponding elements in FIG. 2F, may extend into cap 800. With laser fiber 804 in a first orientation, a first laser beam 812 may be emitted from a side of cap 800 as laser energy is reflected off reflective surface 806 and into lens 808. Laser fiber 804 may be moved (e.g., distally) to a second orientation. In the second orientation, a second laser beam 814 may be emitted from the side of cap 800 as laser energy is reflected off reflective surface 806 and into the other lens 810. It should be understood that features of each of the caps of FIGS. 2A-2H may be used interchangeably with features of any of the other caps of FIGS. 2A-2H.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical system, comprising:
a laser source for providing laser energy;
a fluid source containing a fluid for absorbing the laser energy to generate heat; and
a medical device operatively coupled to the laser source and the fluid source, the medical device including:
a shaft having a distal end,
a cap at the distal end of the shaft, the cap including:
a lens,
a reflector for deflecting the laser energy toward the lens, wherein the lens is configured to emit the laser energy from the cap toward a target,
an aperture configured to emit the fluid from the cap toward the target, and
an opening at a distal end, wherein the opening faces distally and is transverse to the aperture, and
a tube disposed in the shaft, wherein the tube is configured to be extended through the opening to puncture tissue at the target site and emit fluid into the tissue.

2. The medical system of claim 1, wherein the shaft includes a lumen, and wherein the medical system includes a laser emitter optically coupling the medical device to the laser source, the laser emitter extends through the lumen, and the laser emitter includes a laser fiber that extends out of the distal end of the shaft into the cap and delivers laser energy into the cap.

3. The medical system of claim 1, wherein the lens is embedded in a wall of the cap distal to the aperture.

4. The medical system of claim 1, wherein the cap includes a lumen, and the reflector is supported within the lumen by a wall of the cap forming the lumen.

5. The medical system of claim 1, wherein the fluid includes an additive that absorbs a wavelength of light forming part of the laser energy, and wherein the fluid absorbs enough of the laser energy so that the fluid builds heat faster than heat can be dissipated to the external environment.

6. The medical system of claim 1, wherein the shaft includes a lumen in fluid communication with the fluid source, and the aperture of the cap is in fluid communication with the lumen of the shaft.

7. The medical system of claim 6, wherein the fluid flows from the fluid source into the lumen of the shaft, into the lumen of the cap, and out of the aperture of the cap for emission toward the target.

8. The medical system of claim 1, wherein the cap includes a plurality of corrugations extending radially outward from an outer surface of the cap.

9. The medical system of claim 1, wherein the reflector is a first reflector, wherein the cap includes a second reflector distal to the first reflector along a longitudinal axis of the cap, and wherein the first reflector includes a transmission mode, and the first reflector is configured to transmit the laser energy when the first reflector is in the transmission mode.

10. The medical system of claim 9, wherein the laser energy transmitted through the first reflector is configured to be reflected by the second reflector.

11. The medical system of claim 1, wherein the lens includes a plurality of lenses, and wherein the laser energy is configured to be emitted from each of the plurality of lenses.

12. The medical system of claim 1, wherein the reflector includes a plurality of reflectors, and wherein the plurality of reflectors are configured to transmit the laser energy from radially opposite sides of the cap.

13. A medical device, comprising:
a shaft including a distal end;
a cap at the distal end of the shaft, the cap including:
　a lens,
　a reflector for deflecting laser energy toward the lens, wherein the lens is configured to emit laser energy from the cap toward a target,
　an aperture for emitting a fluid from the cap toward the target, and
　an opening at a distal end, wherein the openings faces distally and is transverse to the aperture, and
a tube, wherein the tube is configured to be extended through the opening to puncture tissue at the target site and emit fluid into the tissue.

14. The medical device of claim 13, wherein the lens is embedded in a wall of the cap, and wherein the aperture is located proximal to the lens.

15. The medical device of claim 13, wherein the cap includes a lumen, and the reflector is supported within the lumen by a wall of the cap forming the lumen.

16. The medical device of claim 13, wherein the shaft includes a lumen in fluid communication with and terminating at the aperture.

17. The medical device of claim 13, wherein the aperture is on a radially-outer lateral surface of the cap and spaced from the lens in a direction parallel to a longitudinal axis of the cap.

18. The medical device of claim 13, wherein the lens is one of a plurality of lenses in the cap, and wherein the reflector is one of a plurality of reflectors in the cap.

19. The medical system of claim 13, wherein the reflector includes a transmission mode, and wherein the laser energy is configured to pass through the reflector when the reflector is in the transmission mode.

20. The medical system of claim 13, wherein the reflector includes a plurality of reflectors, and wherein the plurality of reflectors are configured to transmit the laser energy from radially opposite sides of the cap.

* * * * *